United States Patent

Turnbull et al.

[11] Patent Number: 5,246,933
[45] Date of Patent: Sep. 21, 1993

[54] NEMATICIDAL QUINOXALINE DERIVATIVES

[75] Inventors: Michael D. Turnbull; John Finney, both of Earley, England

[73] Assignee: Imperial Chemical Industries PLC, London, England

[21] Appl. No.: 926,012

[22] Filed: Aug. 6, 1992

[30] Foreign Application Priority Data

Aug. 20, 1991 [GB] United Kingdom ............... 9117987

[51] Int. Cl.$^5$ ............... A01N 43/60; C07D 241/44; C07D 241/38
[52] U.S. Cl. .................. 514/249; 544/344; 544/354; 560/20; 560/43
[58] Field of Search .............. 544/354; 514/249

[56] References Cited

U.S. PATENT DOCUMENTS 3,928,608  12/1975  Cox et al. ................ 514/249

FOREIGN PATENT DOCUMENTS 18493  11/1980  European Pat. Off.
432861  6/1991  European Pat. Off.
928494  6/1963  United Kingdom .......... 544/354

OTHER PUBLICATIONS

Derwent Abstract for EP 23785 (Feb. 1981).
Derwent Abstract for DE 3533791 (Mar. 1987).

*Primary Examiner*—Emily Bernhardt
*Attorney, Agent, or Firm*—Joel G. Ackerman

[57] ABSTRACT

Compounds of formula (I)

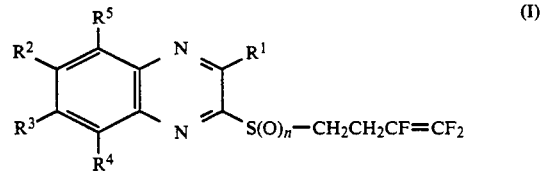

wherein $R^1$, $R^2$, $R^3$, $R^4$ and $R^5$ are independently hydrogen, alkyl, alkenyl, alkynyl, cycloalkyl, alkylcycloalkyl, halogen, haloalkyl, alkoxy, alkenoxy, alkoxyalkyl, haloalkoxy, alkylthio, cyano, nitro, amino, $NR^7R^8$, hydroxy, acylamino, $-CO_2R^6$, phenyl, phenoxy, benzyl or benzyloxy, the phenyl group or phenyl moiety of the benzyl group being optionally substituted; or $R^2$ and $R^3$ when taken together form a 5- or 6-membered ring; $R^6$ and $R^8$ are hydrogen or $C_{1-4}$ alkyl; $R^7$ is $C_{1-4}$ alkyl; and n is 0, 1 or 2: and compositions thereof, are useful for killing or controlling nematodes.

15 Claims, No Drawings

NEMATICIDAL QUINOXALINE DERIVATIVES

The present invention relates to novel quinoxaline derivatives having nematicidal activity, to processes for their preparation, to compositions containing them, and to methods for killing or controlling nematode pests using them.

According to the present invention there is provided a compound of formula (I) wherein $R^1$, $R^2$, $R^3$, $R^4$ and $R^5$ are independently hydrogen, alkyl, alkenyl, alkynyl, cycloalkyl, alkylcycloalkyl, halogen, haloalkyl, alkoxy, alkenoxy, alkoxyalkyl, haloalkoxy, alkylthio, cyano, nitro, amino, $NR^7R^8$, hydroxy, acylamino, $—CO_2R^6$, phenyl, phenoxy, benzyl or benzyloxy, the phenyl group or phenyl moiety of the benzyl group being optionally substituted; or $R^2$ and $R^3$ when taken together form a 5- or 6-membered ring; $R^6$ and $R^8$ are hydrogen or $C_{1-4}$ alkyl; $R^7$ is $C_{1-4}$ alkyl; and n is 0, 1 or 2.

When any one or more of $R^1$, $R^2$, $R^3$, $R^4$ or $R^5$ is an alkyl group it can be straight or branched chain and is preferably $C_{1-4}$ alkyl, in particular methyl, ethyl, propyl, isopropyl, n-butyl, iso-butyl, sec-butyl or tertiary butyl.

When any one or more of $R^1$, $R^2$, $R^3$, $R^4$ or $R^5$ is an alkenyl or alkynyl group it can be straight or branched chain and preferably contains up to 6 carbon atoms, for example, allyl or propargyl.

When any one or more of $R^1$, $R^2$, $R^3$, $R^4$ or $R^5$ is a phenyl, phenoxy, benzyl or benzyloxy group, the phenyl moiety may be optionally substituted with halogen, (for example, chlorine or fluorine), cyano, alkyl, haloalkyl, alkoxy or haloalkoxy, the alkyl group being preferably $C_{1-4}$ alkyl and the alkoxy group being preferably $C_{1-6}$ alkyl. Examples of such groups are 2-, 3- or 4-fluorophenyl, 2-, 3- or 4-chlorophenyl, 2,4- or 2,6-difluorophenyl, 2,4- or 2,6-dichlorophenyl, 2-chloro-4-fluorophenyl, 2-chloro-6-fluorophenyl, 2-fluoro-4-chlorophenyl, 2-fluoro-6-chlorophenyl, 2-,3- or 4-methoxyphenyl, 2,4-dimethoxyphenyl, 2-, 3-, or 4-ethoxyphenyl, 2-, 3- or 4-methylphenyl, 2-, 3- or 4-ethylphenyl, 2-, 3- or 4-trifluoromethylphenyl, and the corresponding ring substituted benzyl, phenoxy and benzyloxy groups.

When any one or more of $R^1$, $R^2$, $R^3$, $R^4$ or $R^5$ is a cycloalkyl or alkylcycloalkyl group, it preferably contains from 3 to 7 carbon atoms, for example, cyclopropyl, cyclopentyl, cyclohexyl or methylcyclopropyl.

When any one or more of $R^1$, $R^2$, $R^3$, $R^4$ or $R^5$ is halogen, it is preferably fluorine or chlorine.

When any one or more of $R^1$, $R^2$, $R^3$, $R^4$ or $R^5$ is haloalkyl, the alkyl moiety is preferably $C_{1-4}$ alkyl, for example, trifluoromethyl, trifluoroethyl or pentafluoroethyl.

When any one or more of $R^1$, $R^2$, $R^3$, $R^4$ or $R^5$ is an alkoxy, alkenoxy or alkoxyalkyl group, it can be straight or branched chain and preferably contains up to 6 carbon atoms, for example, a methoxy, ethoxy, propoxy, butoxy, butenoxy, methoxymethyl, methoxyethyl or ethoxymethyl group.

When any of $R^1$, $R^2$, $R^3$ $R^4$ or $R^5$ is a haloalkoxy group, it can be straight or branched chain and preferably contains up to 6 carbon atoms, for example, trifluoromethoxy, trifluoroethoxy or pentafluoroethoxy.

When any one or more of $R^1$, $R^2$, $R^3$, $R^4$ or $R^5$ is an alkylthio group, the alkyl preferably contains up to 4 carbon atoms. For example, —S-methyl, —S-ethyl, —S-propyl, S-butyl.

When any of $R^1$, $R^2$, $R^3$, $R^4$ or $R^5$ is $NR^7R^8$, it is preferably $NHCH_3$, $N(CH_3)_2$ or $N(C_2H_5)_2$.

When any of $R^1$, $R^2$, $R^3$, $R^4$, or $R^5$ is acylamino, it is preferably $NHCOCH_3$ or $NHCOC_2H_5$.

When any one or more of $R^1$, $R^2$, $R^3$, $R^4$ or $R^5$ is $—CO_2R^6$, $R^6$ is preferably hydrogen, methyl or ethyl.

Preferred compounds of formula (I) are where $R^1$ is hydrogen or $C_{1-4}$ alkyl and $R^2$, $R^3$, $R^4$ and $R^5$ are independently hydrogen, halogen, $C_{1-4}$ alkyl, $C_{1-6}$ alkoxy, $C_{1-4}$ haloalkyl or $C_{1-6}$ haloalkoxy. Particularly preferred are the compounds of formula (I) where two or more of the substituents $R^2$ to $R^5$ are hydrogen, especially those compounds where $R^4$ and $R^5$ are hydrogen. Preferably n is 0.

Examples of the compounds of formula (I) are set out in Table I.

TABLE I

| COMPOUND NO. | $R^1$ | $R^2$ | $R^3$ | $R^4$ | $R^5$ | n |
|---|---|---|---|---|---|---|
| 1 | H | H | H | H | H | 0 |
| 2 | H | H | H | H | H | 2 |
| 3 | $CH_3$ | H | H | H | H | 0 |
| 4 | $CH_3$ | H | H | H | H | 1 |
| 5 | H | F | H | H | H | 0 |
| 6 | H | Cl | H | H | H | 0 |
| 7 | $C_2H_5$ | H | H | H | H | 0 |
| 8 | $C_2H_5$ | H | H | H | H | 1 |
| 9 | $C_2H_5$ | H | H | H | H | 2 |
| 10 | H | Cl | Cl | H | H | 0 |
| 11 | H | H | F | H | H | 0 |
| 12 | H | H | F | H | H | 1 |
| 13 | H | H | F | H | H | 2 |
| 14 | H | H | $C_6H_5$ | H | H | 0 |
| 15 | H | H | $C_6H_5O$ | H | H | 0 |
| 16 | H | H | $C_6H_5CH_2$ | H | H | 0 |
| 17 | H | H | $C_6H_5CH_2O$ | H | H | 0 |
| 18 | H | H | $CH_3O$ | H | H | 0 |
| 19 | H | $CH_3$ | H | H | H | 0 |
| 20 | H | H | $CO_2CH_3$ | H | H | 0 |
| 21 | H | H | $CF_3$ | H | H | 0 |
| 22 | H | H | $CH_3$ | H | H | 0 |
| 23 | H | H | $CH_3$ | H | H | 1 |
| 24 | H | Cl | Cl | Cl | Cl | 0 |
| 25 | H | Cl | Cl | Cl | Cl | 2 |
| 26 | H | H | Cl | Cl | Cl | 0 |
| 27 | H | H | $CF_3$ | H | $CO_2H$ | 0 |
| 28 | H | Cl | H | H | H | 0 |

TABLE I-continued

| COMPOUND NO. | R¹ | R² | R³ | R⁴ | R⁵ | n |
|---|---|---|---|---|---|---|
| 29 | H | Cl | H | H | CN | 0 |
| 30 | H | Cl | H | H | CN | 1 |
| 31 | H | Cl | H | H | $CH_3$ | 0 |
| 32 | H | Cl | H | Cl | H | 0 |
| 33 | H | H | H | $CO_2H$ | H | 0 |
| 34 | H | H | CN | H | H | 0 |
| 35 | H | H | CN | H | H | 2 |
| 36 | H | $CH_3$ | H | H | H | 0 |
| 37 | H | H | H | H | $CO_2CH_3$ | 0 |
| 38 | H | H | $COO_2H$ | H | H | 0 |
| 39 | H | H | $C_6H_5$ | H | H | 0 |
| 40 | H | $CH_3O$ | $CH_3O$ | H | H | 0 |
| 41 | H | H | H | H | Cl | 0 |
| 42 | H | H | F | H | $CH_3$ | 0 |
| 43 | H | H | F | H | $CH_3$ | 2 |
| 44 | H | H | H | Cl | H | 0 |
| 45 | H | H | H | Cl | H | 1 |
| 46 | H | H | Cl | H | H | 1 |
| 47 | H | $CH_3$ | $CH_3O$ | H | H | 0 |
| 48 | H | $CH_3$ | H | H | H | 0 |
| 49 | H | $CH_3$ | $CO_2CH_3$ | H | H | 0 |
| 50 | $CH_3$ | $CH_3$ | $CF_3$ | H | H | 0 |
| 51 | H | $CH_3$ | $CH_3$ | H | H | 0 |
| 52 | H | $CH_3$ | Cl | Cl | Cl | 0 |
| 53 | H | H | $CH_3$ | Cl | Cl | 0 |
| 54 | H | $CH_3$ | $CF_3$ | H | $CO_2H$ | 0 |
| 55 | H | $CH_3$ | H | Cl | H | 0 |
| 56 | H | $CH_3$ | H | Cl | H | 1 |
| 57 | H | $CH_3$ | H | Cl | H | 2 |
| 58 | H | $CH_3$ | H | H | CN | 0 |
| 59 | H | $CH_3$ | H | H | CN | 1 |
| 60 | H | $CH_3$ | H | H | $CH_3$ | 0 |
| 61 | H | $CH_3$ | H | H | $CH_3$ | 1 |
| 62 | $CH_3$ | H | H | $CO_2H$ | H | 0 |
| 63 | $CH_3$ | H | CN | H | H | 0 |
| 64 | $CH_3$ | H | CN | H | H | 2 |
| 65 | $CH_3$ | $CH_3$ | H | H | H | 0 |
| 66 | $CH_3$ | $CH_3$ | H | H | H | 2 |
| 67 | H | $CH_3$ | H | H | $CO_2CH_3$ | 0 |
| 68 | H | $CH_3$ | $CO_2H$ | H | H | 0 |
| 69 | H | $CH_3$ | $C_6H_5$ | H | H | 0 |
| 70 | H | $CH_3$ | $CH_3O$ | H | H | 0 |
| 71 | H | $CH_3$ | $CH_3O$ | H | H | 2 |
| 72 | $CH_3$ | H | H | H | Cl | 0 |
| 73 | $CH_3$ | H | H | H | Cl | 1 |
| 74 | H | $CH_3$ | F | H | $CH_3$ | 0 |
| 75 | $CH_3$ | H | H | Cl | H | 0 |
| 76 | $CH_3$ | H | Cl | H | H | 0 |
| 77 | H | $C_2H_5$ | $CH_3O$ | H | H | 0 |
| 78 | H | $C_2H_5$ | H | H | H | 0 |
| 79 | H | $C_2H_5$ | $CO_2CH_3$ | H | H | 0 |
| 80 | H | $C_2H_5$ | $CF_3$ | H | H | 0 |
| 81 | H | $C_2H_5$ | $CH_3$ | H | H | 0 |
| 82 | $C_2H_5$ | Cl | Cl | Cl | Cl | 0 |
| 83 | $C_2H_5$ | H | Cl | Cl | Cl | 0 |
| 84 | $C_2H_5$ | H | Cl | Cl | Cl | 1 |
| 85 | H | $C_2H_5$ | $CF_3$ | H | $CO_2H$ | 0 |
| 86 | $C_2H_5$ | Cl | H | H | H | 0 |
| 87 | $C_2Hhd 5$ | Cl | H | H | H | 2 |
| 88 | H | $C_2H_5$ | H | H | CN | 0 |
| 89 | H | $C_2H_5$ | H | H | CN | 1 |
| 90 | H | $C_2H_5$ | H | H | $CH_3$ | 0 |
| 91 | H | $C_2H_5$ | H | Cl | H | 0 |
| 92 | H | $C_2H_5$ | H | $CO_2H$ | H | 0 |
| 93 | H | $C_2H_5$ | CN | H | H | 0 |
| 94 | H | H | $C_2H_5$ | H | H | 0 |
| 95 | H | H | $C_2H_5$ | H | H | 1 |
| 96 | H | $C_2H_5$ | H | H | $CO_2CH_3$ | 0 |
| 97 | H | $C_2H_5$ | $CO_2H$ | H | H | 0 |
| 98 | H | $C_2H$ | $C_6H_5$ | H | H | 0 |
| 99 | H | $C_2H_5$ | $CH_3O$ | $CH_3O$ | H | 0 |
| 100 | H | $C_2H_5$ | H | H | Cl | 0 |
| 101 | H | $C_2H_5$ | H | H | Cl | 2 |
| 102 | $C_2H_5$ | H | F | H | $CH_3$ | 0 |
| 103 | $C_2H_5$ | H | H | Cl | H | 0 |
| 104 | $C_2H_5$ | H | H | Cl | H | 1 |
| 105 | H | $C_2H_5$ | Cl | H | H | 0 |
| 106 | H | $CF_3$ | $CH_3O$ | H | H | 0 |
| 107 | H | $CF_3$ | $CH_3$ | H | H | 0 |
| 108 | H | $CF_3$ | $CO_2CH_3$ | H | H | 0 |
| 109 | H | $CF_3$ | H | $CF_3$ | H | 0 |

TABLE I-continued

| COMPOUND NO. | $R^1$ | $R^2$ | $R^3$ | $R^4$ | $R^5$ | n |
|---|---|---|---|---|---|---|
| 110 | $CF_3$ | H | $CH_3$ | H | H | 0 |
| 111 | $CF_3CH_2$ | Cl | Cl | Cl | Cl | 0 |
| 112 | H | $CF_3CH_2$ | Cl | Cl | Cl | 0 |
| 113 | H | $CF_3CH_2$ | Cl | Cl | Cl | 1 |
| 114 | H | $CF_3CH_2$ | $CF_3$ | H | $CO_2H$ | 0 |
| 115 | $CF_3CH_2$ | H | H | H | H | 0 |
| 116 | H | $CF_3CH_2$ | Cl | H | Cl | 0 |
| 117 | H | $CH_3(CH_3)CH$ | H | H | $CH_3$ | 0 |
| 118 | H | $CH_3(CH_3)CH$ | Cl | H | Cl | 0 |
| 119 | H | $CH_3(CH_3)CH$ | Cl | H | Cl | 2 |
| 120 | $CH_3(CH_3)CH$ | H | H | H | H | 0 |
| 121 | H | $CH_3(CH_3)CH$ | Cl | H | H | 0 |
| 122 | H | $CH_3(CH_3)CH$ | $CH_3$ | H | H | 0 |
| 123 | H | $CH_3(CH_3)CH$ | $CH_3$ | H | H | 1 |
| 124 | $C_2H_5(CH_3)CH$ | H | H | H | H | 0 |
| 125 | H | $C_2H_5(CH_3)CH$ | $CO_2H$ | H | H | 0 |
| 126 | H | $C_2H_5(CH_3)CH$ | H | Cl | H | 0 |
| 127 | H | $C_2H_5(CH_3)CH$ | H | Cl | H | 2 |
| 128 | H | $C_2H_5(CH_3)CH$ | $CH_3O$ | $CH_3O$ | H | 0 |
| 129 | H | $C_2H_5(CH_3)CH$ | H | H | Cl | 0 |
| 130 | H | $C_2H_5(CH_3)CH$ | H | H | Cl | 1 |
| 131 | H | $CH_3(CH_3)CHCH_2$ | F | H | H | 0 |
| 132 | H | $CH_3(CH_3)CHCH_2$ | H | Cl | H | 0 |
| 133 | H | $CH_2CH=CH_2$ | H | H | H | 0 |
| 134 | H | H | Cl | H | H | 0 |
| 135 | H | H | $^cC_3H_5$ | H | H | 0 |
| 136 | H | H | $1\text{-}CH_3\text{—}^cC_3H_5$ | H | H | 0 |
| 137 | H | H | $SCH_3$ | H | H | 0 |
| 138 | H | H | OH | H | H | 0 |
| 139 | H | H | $4\text{-}F\text{-}C_6H_4$ | H | H | 0 |
| 140 | H | H | $-C\equiv CH$ | H | H | 0 |
| 141 | H | H | $-OCH_2CF_3$ | H | H | 0 |
| 142 | H | H | $-(CH_2)_3-$ | H | H | 0 |
| 143 | H | H | $-(CH_2)_4-$ | H | H | 0 |
| 144 | H | $-CH=CH-CH=CH-$ | H | H | 0 | |
| 145 | H | H | $NHCH_3$ | H | H | 0 |
| 146 | H | H | $NHCOCH_3$ | H | H | 0 |
| 147 | H | H | $-C(CH_3)_3$ | H | H | 0 |
| 148 | H | H | $-CH_2OCH_3$ | H | H | 0 |
| 149 | H | H | $4\text{-}CF_3\text{—}C_6H_4CH_2$ | H | H | 0 |
| 150 | H | H | $NH_2$ | H | H | 0 |

The compounds of formula (I) where $R^1$ to $R^5$ have the meanings defined above and n is 0, are prepared by reacting a correspondingly substituted 2-mercaptoquinoxaline of formula (II) with 4-bromo-1,1,2-trifluorobut-1-ene in the presence of a base such as a carbonate, for example, potassium carbonate, and an inert solvent, for example acetone. Both the compounds of formula (II) and 4-bromo-1,1,2-trifluoro-but-1-ene can be obtained by conventional methods or from commercial sources.

Thus according to a further aspect of the present invention there is provided a process for the preparation of compounds of formula (I) where n is 0 and $R^1$, $R^2$, $R^3$, $R^4$ and $R^5$ have the meanings defined above which comprises reacting a correspondingly substituted compound of formula (II) which 4-bromo-1,1,2-trifluorobut-1-ene in the presence of a base.

The compounds of formula (I) where any one or more of $R^1$, $R^2$, $R^3$, $R^4$ or $R^5$ is alkoxy can alternatively be prepared by reacting the corresponding hydroxy derivative of formula (I) with an alkylating agent, for example, dimethyl sulphate.

The compounds of formula (I) where $R^1$ to $R^5$ have the meanings defined above and n is 1 or 2, are prepared by reacting a correspondingly substituted compound of formula (I) where n is 0 with an oxidising agent. The oxidation is carried out using conventional methods, for example, by treatment with a peroxide in an inert organic solvent. Suitable peroxides include organic peroxides such as peroxy carboxylic acids, or their salts, for example, the magnesium salt of monoperoxyphthalic acid. Suitable inorganic peroxides include potassium peroxymono-sulphate.

Thus according to a yet further aspect of the present invention there is provided a process for the preparation of compounds of formula (I) where n is 1 and $R^1$, $R^2$, $R^3$, $R^4$ and $R^5$ have the meanings defined above, which comprises reacting a correspondingly substituted compound of formula (I) when n is 0, with an oxidising agent.

The compounds of formula (I) are nematicidal and can be used to control nematodes in crop plants. Therefore, in a further aspect of the invention, there is provided a method of killing or controlling nematodes which comprises applying to the locus of the pests or to a plant susceptible to attack by the pest an effective amount of a compound of formula (I) as defined herein or a composition containing a compound of formula (I) as defined herein.

The term "controlling" extends to non-lethal effects which results in the prevention of damage to the host plant and the limitation of nematode population increase. These effects may be the result of chemical induced disorientation, immobilisation, or hatch prevention or induction. The chemical treatment may also have deleterious effects on nematode development or reproduction.

The compounds of the invention can be used against both plant-parasitic nematodes and nematodes living freely in the soil. Examples of plant-parasitic nematodes are: ectoparasites, for example Xiphinema spp., Longidorus spp. and Trichodorous spp.; semi-endoparasites, for example, Tylenchulus spp.; migratory endoparasites, for example, Pratylenchus spp., Radopholus spp. and Scutellonema spp.; sedentary endoparasites, for example, Heterodera spp., Globodera spp. and Meloidogyne spp.; and stem and leaf endoparasites, for example, Ditylenchus spp., Aphelenchoides spp. and Hirshmaniella spp..

The compounds of the invention can also be used in combating a range of insects and acarids. Examples include Lepidoptera, Diptera, Homoptera, Coleoptera (including Diabrotica i.e. corn rootworms).

In order to apply the compound to the locus of the nematode or to a plant susceptible to attack by the nematode, the compound is usually formulated into a composition which includes in addition to the compound of formula (I) suitable inert diluent or carrier materials, and/or surface active agents. Thus in a further aspect of the invention there is provided a nematicidal composition comprising an effective amount of a compound of formula (I) as defined herein and an inert diluent or carrier material and optionally a surface active agent.

The amount of composition generally applied gives a rate of active ingredient from 0.01 to 10 kg per hectare, preferably from 0.1 to 6 kg per hectare.

The compositions can be applied to the soil, plant or seed, in the form of dusting powders, wettable powders, granules (slow or fast release), emulsion or suspension concentrates, liquid solutions, emulsions, seed dressings, fogging/smoke formulations or controlled release compositions, such as microencapsulated granules or suspensions.

Dusting powders are formulated by mixing the active ingredient with one or more finely divided solid carriers and/or diluents, for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers.

Granules are formed either by absorbing the active ingredient in a porous granular material for example pumice, attapulgite clays, fuller's earth, kieselguhr, diatomaceous earths, ground corn cobs, and the like, or on to hard core materials such as sands, silicates, mineral carbonates, sulphates, phosphates, or the like. Agents which are commonly used to aid in impregnation, binding or coating the solid carriers include aliphatic and aromatic petroleum solvents, alcohols, polyvinyl acetates, polyvinyl alcohols, ethers, ketones, esters, dextrins, sugars and vegetable oils. with the active ingredient. Other additives may also be included, such as emulsifying agents, wetting agents or dispersing agents.

Microencapsulated formulations (microcapsule suspensions CS) or other controlled release formulations may also be used, particularly for slow release over a period of time, and for seed treatment.

Alternatively the compositions may be in the form of liquid preparations to be used as dips, irrigation additives or sprays, which are generally aqueous dispersions or emulsions of the active ingredient in the presence of one or more known wetting agents, dispersing agents or emulsifying agents (surface active agents). The compositions which are to be used in the form of aqueous dispersions or emulsions are generally supplied in the form of an emulsifiable concentrate (EC) or a suspension concentrate (SC) containing a high proportion of the active ingredient or ingredients. An EC is a homogeneous liquid composition, usually containing the active ingredient dissolved in a substantially non-volatile organic solvent. An SC is a fine particle size dispersion of solid active ingredient in water. To apply the concentrates they are diluted in water and are usually applied by means of a spray to the area to be treated.

Suitable liquid solvents for ECs include methyl ketone, methyl isobutyl ketone, cyclohexanone, xylenes, toluene, chlorobenzene, paraffins, kerosene, white oil, alcohols, (for example, butanol), methylnaphthalene, trimethylbenzene, trichloroethylene, N-methyl-2-pyrrolidone and tetrahydrofurfuryl alcohol (THFA).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

These concentrations are often required to withstand storage for prolonged periods and after such storage, to be capable of dilution with water to form aqueous preparations which remain homogeneous for a sufficient time to enable them to be applied by conventional spray equipment. The concentrates may contain 10-85% by weight of the active ingredient or ingredients. When diluted to form aqueous preparations such preparations may contain varying amounts of the active ingredient depending upon the purpose for which they are to be used.

The compounds of formula (I) may also be formulated as powders (dry seed treatment DS or water dispersible powder WS) or liquids (flowable concentrate FS, liquid seed treatment LS, or microcapsule suspension CS) for use in seed treatments. In use the compositions are applied to the nematodes, to the locus of the nematodes, to the habitat of the nematodes, or to growing plants liable to infestation by the nematodes, by any of the known means of applying pesticidal compositions, for example, by dusting, spraying, or incorporation of granules.

The compounds of the invention may be the sole active ingredient of the composition or they may be admixed with one or more additional active ingredients such as nematicides or agents which modify the behaviour of nematodes such as hatching factors, insecticides, synergists, herbicides, fungicides or plant growth regulators where appropriate.

Suitable additional active ingredients for inclusion in admixture with the compounds of the invention may be compounds which will broaden the spectrum of activity of the compounds of the invention or increase their persistence in the location of the pest. They may synergise the activity of the compound of the invention or complement the activity for example by increasing the speed of effect or overcoming repellency. Additionally multi-component mixtures of this type may help to overcome or prevent the development of resistance to individual components.

The particular additional active ingredient included will depend upon the intended utility of the mixture and the type of complementary action required. Examples of suitable insecticides include the following:

a) Pyrethroids such as permethrin, esfenvalerate, deltamethrin, cyhalothrin in particular lambda-cyhalothrin, biphenthrin, fenpropathrin, cyfluthrin, tefluthrin, fish safe pyrethroids for example ethofenprox, natural pyrethrin, tetramethrin, s-bioallethrin, fenfluthrin, prallethrin and 5-benzyl-3-furylmethyl-(E)-(1R,3S)-2,2-dimethyl-3-(2-oxothiolan-3-ylidenemethyl) cyclopropane carboxylate;

b) Organophosphates such as profenofos, sulprofos, methyl parathion, azinphos-methyl, demeton-s-methyl, heptenophos, thiometon, fenamiphos, monocrotophos, profenophos, triazophos, methamidophos, dimethoate, phosphamidon, malathio, chloropyrifos, phosalone, terbufos, fensulfothion, fonofos, phorate, phoxim, pyrimiphos-methyl, pyrimiphos-ethyl, fenitrothion or diazionon;

c) Carbamates (including aryl carbamates) such as pirimicarb, cloethocarb, carbofuran, furathiocarb, ethiofencarb, aldicarb, thiofurox, carbosulfan, bendiocarb, fenobucarb, propoxur or oxamyl;

d) Benzoyl ureas such as triflumuron, or chlorofluazuron;

e) Organic tin compounds such as cyhexatin, fenbutatin oxide, azocyclotin;

f) Macrolides such as avermectins or milbemycins, for example such as abamectin, avermectin, and milbemycin;

g) Hormones and pheromones;

h) Organochlorine compounds such as benzene hexachloride, DDT, chlordane or dieldrin;

i) Amidines, such as chlordimeform or amitraz;

j) Fumigant agents.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin can be employed. Alternatively insecticides specific for particular insect species/stages for example ovo-larvicides such as chlofentezine, flubenzimine, hexythiazox and tetradifon, moltilicides such as dicofol or propargite, acaricides such as bromopropylate, chlorobenzilate, or growth regulators such as hydramethylon, cyromazin, methoprene, chlorofluazuron and diflubenzuron may also be included in the compositions.

Examples of suitable synergists for use in the compositions include piperonyl butoxide, sesamax, safroxan and dodecyl imidazole.

Suitable herbicides, fungicides and plant-growth regulators for inclusion in the compositions will depend upon the intended target and the effect required.

An example of a rice selective herbicides which can be included is propanil, an example of a plant growth regulator for use in cotton is "Pix", and examples of fungicides for use in rice include blasticides such as blasticidin-S. The ratio of the compound of the invention to the other active ingredient in the composition will depend upon a number of factors including type of target, effect required from the mixture etc. However in general, the additional active ingredient of the composition will be applied at about the rate as it is usually employed, or at a slightly lower rate if synergism occurs.

The following Examples illustrate the invention. The starting materials can be prepared by methods known in the art or obtained commercially. The compounds were identified and characterised by means of their melting points, nuclear magnetic resonance spectroscopy ($^1$H NMR $\delta$ (CDCl$_3$)), and/or mass spectroscopy.

EXAMPLE 1

This example illustrates the preparation of Compound No. 1 of Table I.

Step a: Preparation of 2-mercaptoquinoxaline.

2-Chloroquinoxaline (2 g) and sodium hydrosulphide (1.23 g) were stirred together in 25 ml of dimethylformamide and heated to 100° C. After 3 hours the reaction mixture was allowed to cool and then partitioned between 70 ml of water and 30 ml of ethyl acetate. The organic layer was separated and the aqueous layer extracted twice with 20 ml of ethyl acetate. The combined organic extracts were washed with sodium chloride solution, dried over anhydrous magnesium sulphate, filtered and the solvent removed under reduced pressure to yield an orange solid (3.1 g). The product of this reaction was used in the next preparative step without further purification.

Step b:

The product of step a (3.1 g) was dissolved in acetone and potassium carbonate (1.66 g) added in a single portion. The reaction mixture was heated to reflux and 4-bromo-1,1,2-trifluorobut-1-ene (2.3 g) added dropwise.

After 2 hours the reaction mixture was allowed to cool, filtered to remove insoluble potassium salts and the filtrate evaporated under reduced pressure to yield a brown oil. The oil was subjected to chromatography through silica using ethyl acetate/hexane (1:19) as eluent to yield 1.4 g (43%) of a yellow oil.

Compound Nos. 5, 6, 7 and 10 of Table 1 were prepared by analogy using the preparative route of Example 1.

| Compound No. | M. Pt (°C.) | M+ | NMR |
|---|---|---|---|
| 1 | | 270 | 2.75–2.95(m, 2H); 3.50(t, 2H); 7.58–7.78(m, 2H); 7.95(t, 1H); 8.05 (t, 1H); 8.60(s, 1H) |
| 5 | 72.8–73.8 | 288 | 2.73–2.93(m, 2H); 3.50(t, 2H); 7.50 (t, 1H); 7.65(t, 1H); 7.90(t, 1H); 8.60(s, 1H) |
| 6 | 54.6–55.5 | | 2.75–2.90(m, 2H); 3.50(t, 2H); 7.65 (m, 1H); 7.85(d, 1H); 8.05(d, 1H); 8.40(s, 1H) |
| 7 | 42.4–43.1 | 298 | 1.43(t, 3H); 2.74–2.92(m, 2H); 2.98 (q, 2H); 3.40(t, 2H); 7.63(m, 2H); 7.90(dd, 1H); 7.99(dd, 1H) |
| 10 | 56–57.5 | 338 | 2.73–2.90(m, 2H); 3.49(t, 2H); 8.04 (s, 1H); 8.14(s, 1H); 8.57(s, 1H) |

EXAMPLE 2

This example illustrates the preparation of Compound No. 2 of Table I.

Compound No. 1 from Example 1 (0.5 g) was stirred in 10 ml of ethanol at room temperature. A solution of the magnesium salt of monoperoxyphthalic acid (0.99 g) in 5 ml of water was added dropwise and the reaction heated to 70° C.

After 2 hours the reaction mixture was cooled and partitioned between 30 ml of a saturated sodium bicarbonate solution and 10 ml of ethyl acetate. The organic layer was separated and the aqueous layer was extracted with 5 ml of ethyl acetate. The combined organic extracts were washed with dilute sodium bicarbonate solution, dried over anhydrous magnesium sulphate, filtered, and the solvent removed under reduced pressure to yield a white solid. The solid was subjected to chromatography through silica using ethyl acetate/hexane (1:19) as eluent to yield 0.13 g (22%) of a white solid.

Compound Nos. 4, 8, 9, 12 and 13 of Table I are prepared by analogy using the preparative route of Example 2.

| Compound No. | M. Pt (°C.) | M+ | NMR |
|---|---|---|---|
| 2 | 84.3–85.6 | 302 | 2.88–3.10(m, 2H); 3.80(t, 2H); 7.90–8.10(m, 2H); 8.20–8.30(m, 2H); 9.50(s, 1H) |
| 4 | | 300 | 2.78–3.10(m, 2H); 3.00(s, 3H); 3.30–3.50(m, 2H); 7.80–7.90(m, 2H); 8.10(d, 1H); 8.20(d, 1H) |
| 8 | 92.3–92.8 | 314 | 1.50(t, 3H); 2.72–3.12(m, 2H); 3.27 (q, 2H); 3.32–3.55(m, 2H); 7.84 (m, 2H); 8.13(dd, 1H); 8.21(dd, 1H) |
| 9 | 54.6–55.5 | 330 | 1.51(t, 3H); 2.98–3.17(m, 2H); 3.48 (q, 2H); 4.00(t, 2H); 7.79–7.97 (m, 2H); 8.07(d, 1H); 8.15(d, 1H) |
| 12 | 98.6–99.2 | 304 | 2.55–2.78(m, 1H); 2.85–3.10(m, 1H); 3.31–3.57(m, 2H); 7.64–7.78(m, 2H); 8.26(q, 1H); 9.42(s, 1H) |
| 13 | 60.4–61.0 | 320 | 2.85–3.05(m, 2H); 3.79(t, 2H); 7.75–7.87(m, 2H); 8.29(q, 1H); 9.48(s, 1H) |

EXAMPLE 3

This example illustrates the preparation of Compound No. 3 of Table 1.

Step a: Preparation of 2-mercapto-3-methylquinoxaline

2-Hydroxy-3-methylquinoxaline (2 g) and phosphorus pentasulphide (3.05 g) were stirred together in 40 ml of pyridine and the reaction mixture heated to reflux.

After 4 hours the reaction mixture was allowed to cool and the pyridine removed under reduced pressure. The residue was partitioned between 150 ml of water and 50 ml of ethyl acetate. The organic layer was separated and the aqueous layer was extracted twice with 30 ml of ethyl acetate. The combined organic extracts were washed with water, dried over anhydrous magnesium sulphate, filtered, and the solvent removed under reduced pressure to yield 1.3 g (60%) of a brown solid. The product of this reaction was used in the next preparative step without further purification.

Step b: The product of Step a (1.3 g) was treated as described in Step b of Example 1. The reaction yielded 1.47 g (70%) of a brown solid.

| Compound No. | M. Pt (°C.) | M+ | NMR |
|---|---|---|---|
| 3 | 50–51 | 284 | 2.65(s, 3H); 2.75–2.95(m, 2H); 3.50 (t, 2H); 7.59–7.70(m, 2H); 7.88–7.98 (m, 2H) |

EXAMPLE 4

This example illustrates the preparation of compound no. 11 of Table 1

Step a: Preparation of Ethyl N-(4-fluorophenyl)glycine.

4-Fluoroaniline (5 g), potassium carbonate (3.11 g) and a catalytic amount of 18-Crown-6 were stirred together in 50 ml of ethanol. A solution of ethylbromoacetate (7.52 g) in 25 ml of ethanol was added dropwise and the reaction was heated to reflux.

After 2 hours the reaction was allowed to cool, filtered to remove insoluble potassium salts and the filtrate was evaporated under reduced pressure to yield 9.2 g of a brown solid.

Step b: Preparation of Ethyl N-(4-fluoro-2-nitrophenyl)glycine.

The product of step a (5.2 g) was dissolved in 50 ml of dichloromethane and a solution of fuming nitric acid (3.6 ml) in 6 ml dichloromethane was added in three portions. After 50 hours the reaction mixture was poured into 100 ml water and the organic layer was separated. The aqueous layer was extracted with 30 ml of dichloromethane and the combined organic extracts were washed with water, dried over anhydrous magnesium sulphate filtered through silica and the solvent removed under reduced pressure to yield an orange solid (2.75 g).

Step c

The product of step b (2.75 g) was dissolved in 50 ml of isopropanol. Iron powder (5 g), water (30 ml) and concentrated hydrochloric acid (4 drops) were added and the reaction mixture was heated to 80° C.

After 5 hours the reaction was allowed to cool, filtered through celite and the filtrate was partitioned between 100 ml water and 40 ml ethyl acetate. The organic layer was separated and the aqueous layer was extracted twice with 30 ml of ethyl acetate. The combined organic extracts were washed with water, dried over anhydrous magnesium sulphate, filtered and the solvent removed under reduced pressure to yield a brown solid. The solid was subjected to silica chromatography eluted with ethyl acetate/hexane (3:7 initially, increasing to 1:1) to yield 0.83 g of a cream solid.

Step d

The product of step C (0.83 g) was dissolved in 2M sodium hydroxide (20 ml) and 30% hydrogen peroxide (7.5 ml) was added. The reaction mixture was heated to 100° C.

After 1 hour the reaction was allowed to cool and then acidified to pH4 using concentrated hydrochloric acid. Precipitated solid was filtered off and combined with organic extracts of the acidic solution (3×20 ml ethyl acetate), dried over anhydrous magnesium sulphate, filtered and the solvent removed under reduced pressure to yield a brown solid (0.62 g).

Step e

The product of step d was treated as described in Example 3 to give 0.98 g of a yellow oil.

| Compound No. | M. Pt (°C.) | M+ | NMR |
|---|---|---|---|
| 11 | | 288 | 2.71–2.91(m, 2H); 3.50(t, 2H); 7.42 (dt, 1H); 7.56(dd, 1H); 8.03(m, 1H); 8.55(s, 1H) |

EXAMPLE 5

In order to illustrate the nematicidal properties of the compounds of formula (I), compounds from Table I were tested on root knot nematodes and cyst nematodes.

Methodology

Test A: Cucumber plants (9 days old, variety 'Telegraph') were soil drenched with a composition of a compound of formula (I) (obtained by diluting 1 part of a solution of the compound in a 1:1 mixture of acetone and ethanol with 99 parts of water containing 0.05% of a wetting agent) at a rate of 40 ppm in a drench volume of 10 ml/45 g of soil. The plants were infested with second stage juveniles of the root knot nematode *Meloidogyne incognita* after the solution of the compound had been absorbed by the soil. Nematodes were applied to the roots in a solution of water. The roots of the plants were examined after 9 days to determine the percentage reduction in the number of root knots compated with a control treatment omitting the compound. There were 3 replicates per treatment.

Test B: Tomato plants (6–8 weeks old, variety 'Moneymaker') were planted out into soil infested with second stage juveniles of the root knot nematode *Meloidogyne incognita*. The soil was drenched with a composition of a compound of formula (I) (obtained by diluting 1 part of a solution of the compound in a 1:1 mixture of acetone and ethanol with 99 parts of water containing 0.05% of a wetting agent) at a rate of 2.5 or 1.25 ppm in a drench volume of 200 ml/kg of soil. The roots of the plants were examined after 3 weeks to determine the percentage reduction in the number of root knots compared with a control treatment omitting the compound. There were 3 replicates per treatment.

Test C: Tomato plants (6–8 weeks old, variety 'Moneymaker') were transplanted into soil infested with potato cyst nematode (*Globodera rostochiensis*). The soil was drenched with a composition of a compound of formula (I) (obtained by diluting 1 part of a solution of the compound in a 1:1 mixture of acetone and ethanol with 99 parts of water containing 0.05% of a wetting agent) at a rate of 10 or 20 ppm in a drench volume of 266 ml/kg of soil. The cysts were extracted from the soil after 8 weeks by flotation and percentage reduction in the number of cysts compared with a control treatment omitting the compound was determined. There were 5 replicates per treatment. The results are given in Table II. In the table a blank indicates less than 25% reduction, a hyphen indicates no test carried out at that rate.

The compounds of the invention display nematicidal activity against different types of nematodes including the cyst nematode. A further advantage is that the compounds are not phytotoxic to the target plant. Very little phytotoxicity was observed in the above tests. This is a particularly desirable feature when treating young plants and seeds.

TABLE II

| | % ROOT KNOT REDUCTION | | | % CYST REDUCTION | |
|---|---|---|---|---|---|
| | APPLICATION RATE (PPM) | | | | |
| COMPOUND NO. | 40 | 2.5 | 1.25 | 20 | 10 |
| 1 | 94 | 56 | 21 | — | — |
| 2 | 96 | 93 | 65 | 90 | — |
| 4 | 96 | 88 | | 74 | — |
| 5 | 98 | | | — | — |
| 6 | 97 | 85 | 51 | 100 | 100 |
| 8 | 99 | | | — | — |
| 9 | 98 | | | — | — |
| 10 | 100 | 74 | 44 | 80 | — |
| 11 | 95 | — | — | — | — |
| 12 | 89 | — | — | — | — |
| 13 | 89 | — | — | — | — |

The following examples demonstrate formulations suitable for applying the compounds of the present invention. The amount of ingredient is expressed in parts by weight or grams per liter as indicated. * indicates a trademark.

EXAMPLE 6

This example demonstrates granules suitable for soil application. The granules can be made be standard techniques such as impregnation, coating, extrusion or agglomeration.

| | | % w/w |
|---|---|---|
| Impregnated granule: | Active ingredient | 5 |
| | Wood Rosin | 2.5 |
| | Gypsum granules (20–40 mesh) | 92.5 |
| Coated granule: | Active ingredient | 0.5 |
| | Solvesso* 200 | 0.4 |
| | Calcium carbonate granules (30–60 mesh) | 99.1 |
| Slow release granule: | Active ingredient | 10 |
| | Polyvinylacetate/vinyl chloride copolymer latex | 5 |
| | Attapulgus granules | 85 |

EXAMPLE 7

This example demonstrates formulations for use as a spray. The compounds can be formulated as wettable powders, water dispersible granules, suspension concentrates, emulsifiable concentrates, emulsions or microcapsule suspensions for application diluted in water.

| | | g/l |
|---|---|---|
| Emulsifiable concentrate: | Active ingredient | 250 |
| | Calcium dodecylbenzene sulphonate | 50 |
| | Nonyl phenol ethoxylate | 50 |
| Wettable powder: | Liquid active ingredient | 40 |
| | lignosulphonate dispersant | 5 |
| | silica | 25 |
| | sodium lauryl sulphate | 3 |
| | china clay (kaolin) | 27 |
| Microcapsule suspension: | Liquid active ingredient | 250 |
| | toluene diisocyanate | 10 |
| | polymethylene polyphenyl isocyanate | 20 |
| | nonyl phenol ethoxylate | 6 |
| | lignosulphonate dispersant | 15 |
| | xanthan gum | 1 |
| | bentonite | 10 |
| | biocide 'Proxel'* | 0.1 |
| | sodium carbonate | 5 |

| | g/l |
|---|---|
| water | to 1 liter |

The microcapsule suspensions can be used as a spray, soil drench or as an intermediate to prepare slow release granules for application to the soil.

| | | g/l |
|---|---|---|
| Suspension concentrate: | Solid active ingredient | 400 |
| | lignosulphonate dispersant | 50 |
| | sodium lauryl sulphate | 30 |
| | xanthan gum | 1 |
| | biocide 'Proxel'* | 0.1 |
| | bentonite | 10 |
| | water | to 1 liter |

EXAMPLE 8

This example demonstrates formulations suitable for use as seed treatments in conventional application machinery.

| | | % w/w |
|---|---|---|
| Dry seed treatment: | Active ingredient | 20 |
| | dodecyl benzene | 3 |
| | Rubine Toner (dyestuff) | 2.7 |
| | talc | 53.3 |
| | Silica | to 100% |

The suspension concentrate and microcapsule suspension of Example 8 can be used as flowable concentrates for seed treatment.

EXAMPLE 9

This example demonstrates the formulation of the compounds for electrostatic spraying.

| | g/l |
|---|---|
| Active ingredient | 200 |
| N-methylpyrollidone | 50 |
| Soyabean oil | 120 |
| 'Solvesso' 200 | to 1 liter |

CHEMICAL FORMULAE (corresponding to formulae numbers given the description)

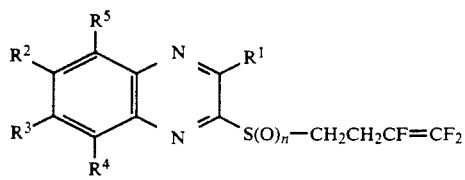
(I)

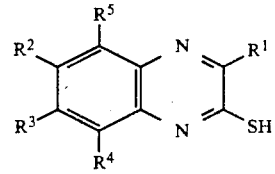
(II)

We claim:

1. A compound of formula (I):

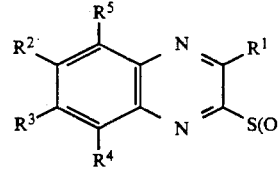
(I)

wherein $R^1$, $R^2$, $R^3$, $R^4$ and $R^5$ are independently hydrogen, $C_{1-4}$ alkyl, $C_{2-6}$ alkenyl, $C_{2-6}$ alkynyl, $C_{3-7}$ cycloalkyl, $(C_1-C_4)$alkyl $C_{3-7}$ cycloalkyl, halogen, halo-$(C_{1-4})$alkyl, $C_{1-6}$ alkoxy, $C_{2-6}$ alkenoxy, $C_{2-6}$ alkoxyalkyl, halo-$(C_{1-6})$alkoxy, $C_{1-4}$ alkylthio, cyano, nitro, amino, $NR^7R^8$, hydroxy, $C_{2-3}$ acylamino, $-CO_2R^6$, phenyl, phenoxy, benzyl or benzyloxy, the phenyl group or phenyl moiety of the benzyl group being optionally substituted with halogen, cyano, $C_{1-4}$ alkyl, halo-$(C_{1-4})$alkyl, $C_{1-6}$ alkoxy or halo-$(C_{1-6})$alkoxy; $R^6$ and $R^8$ are hydrogen or $C_{1-4}$ alkyl; $R^7$ is $C_{1-4}$ alkyl; and n is 0, 1 or 2.

2. A compound according to claim 1 wherein $R^1$ is hydrogen or alkyl.

3. A compound according to claim 1 or 2 wherein $R^2$, $R^3$, $R^4$ and $R^5$ are independently hydrogen, halogen, alkyl, alkoxy or haloalkoxy.

4. A compound according to any of the preceding claims wherein two or more of the substituents $R^2$, $R^3$, $R^4$ and $R^5$ are hydrogen.

5. A compound according to any of the preceding claims wherein $R^4$ and $R^5$ are both hydrogen.

6. A compound according to any of the preceding claims wherein $R^3$ is halogen.

7. A compound according to any of the preceding claims wherein n is 0.

8. A compound according to any of the preceding claims wherein n is 1.

9. A compound according to any of the preceding claims wherein n is 2.

10. A compound according to claim 1 wherein $R^1$ is hydrogen or $C_{1-4}$ alkyl; $R^2$, $R^3$, $R^4$ and $R^5$ are independently hydrogen, halogen, $C_{1-4}$ alkyl, $C_{1-6}$ alkoxy, $C_{1-4}$ haloalkyl or $C_{1-6}$ haloalkoxy; and n is 0.

11. A compound according to claim 10 wherein R2 is halogen, $C_{1-4}$ alkyl, $C_{1-6}$ alkoxy, $C_{1-4}$ haloalkyl or $C_{1-6}$ haloalkoxy; and $R^3$, $R^4$ and $R^5$ are hydrogen.

12. A compound according to claim 10 wherein $R^3$ is halogen, $C_{1-4}$ alkyl, $C_{1-6}$ alkoxy, $C_{1-4}$ haloalkyl or $C_{1-6}$ haloalkoxy; and $R^2$, $R^4$ and $R^5$ are hydrogen.

13. A compound according to claim 10 wherein $R^1$, $R^2$, $R^4$ and $R^5$ are hydrogen, $R^3$ is fluorine or chlorine and n is 0.

14. A nematicidal composition comprising an effective amount of a compound of formula (I) as defined in claim 1 and an inert diluent or carrier material and optionally a surface active agent.

15. A method of killing or controlling nematode pests which comprises applying to the locus of the pests or to a plant susceptible to attack by the pest an effective amount of a compound of formula (I) as defined in claim 1 or a composition as defined in claim 14.

* * * * *